United States Patent [19]

Burnham et al.

[11] Patent Number: 5,193,383
[45] Date of Patent: Mar. 16, 1993

[54] MECHANICAL AND SURFACE FORCE NANOPROBE

[75] Inventors: Nancy A. Burnham, Alexandria; Richard J. Colton, Springfield, both of Va.

[73] Assignee: The United States of America as represented by the Secretary of the Navy, Washington, D.C.

[21] Appl. No.: 560,391

[22] Filed: Jul. 11, 1990

[51] Int. Cl.$^5$ .................... G01B 21/30; G01B 7/34; G01N 13/00; G01N 3/40
[52] U.S. Cl. ........................... 73/105; 73/81; 250/307
[58] Field of Search ............... 73/105, 81; 250/306, 250/307

[56] References Cited

U.S. PATENT DOCUMENTS

| Re. 33,387 | 10/1990 | Binnig | 250/306 |
|---|---|---|---|
| 3,303,674 | 2/1967 | D'Onofrio | 73/862.59 X |
| 4,083,236 | 4/1978 | Steinmueller | 73/862.52 |
| 4,103,545 | 8/1978 | Rykwalder et al. | 177/229 X |
| 4,162,632 | 7/1979 | Steinmueller | 73/862.62 X |
| 4,472,976 | 9/1984 | Bonfils et al. | 73/862.62 |
| 4,806,755 | 2/1989 | Duerig et al. | 250/423 F X |
| 4,861,990 | 8/1989 | Coley | 250/306 |
| 4,883,959 | 11/1989 | Hosoki et al. | 250/306 |
| 4,935,634 | 6/1990 | Hansma et al. | 250/306 X |
| 4,987,303 | 1/1991 | Takase et al. | 250/306 |
| 5,003,815 | 4/1991 | Martin et al. | 73/105 |
| 5,036,196 | 7/1991 | Hosaka et al. | 250/306 |

OTHER PUBLICATIONS

"Probing the Surface Forces of Monolayer Films with an Atomic-Force Microscope"; *Physical Review Letters* vol. 64, No. 16, pp. 1931-1934; Nancy A. Burnham, Dominguez, Mowery, and Colton, Apr. 16, 1990.
"Measuring the nanomechanical properties and surface forces of materials using an atomic force microscope" *J. Vac. Sci. Techol. A,* vol. 7, No. 4, Jul./Aug. 1989, pp. 2906-2913; Burnham and Colton.
G. Binnig & C. Quate, Atomic Force Microscope, Physical Review Ltrs., vol. 56 No. 9, Mar. 3, 1986 1 pp. 930-933.
T. Albright & C. Quate, Atomic Resolution Imaging of a Nonconductor by Atomic Force Microscope, J. Appl Phys 62(7), Oct. 1, 1987, pp. 2599-2602.

*Primary Examiner*—Tom Noland
*Attorney, Agent, or Firm*—Thomas E. McDonnell; Larry A. Root; Charles J. Stockstill

[57] ABSTRACT

A method and apparatus to use an Atomic Force Microscope to take measurements of surface forces, indentation, adhesion and mechanical properties such as hardness and elasticity. The force between a probe mounted cantilever and a sample is measured as a function cantilever deflection measured by a electron tunneling microscope. The sample and the tip of the tunneling microscope are each mounted on piezoelectric manipulators which provide for position control. Position of the sample and probe are measured from the voltages applied to the piezoelectric manipulators. Penetration is determined by the relative motion between the probe and sample. Presently, this invention has a force resolution of 1 nN and a depth resolution of 0.02 nm.

6 Claims, 2 Drawing Sheets

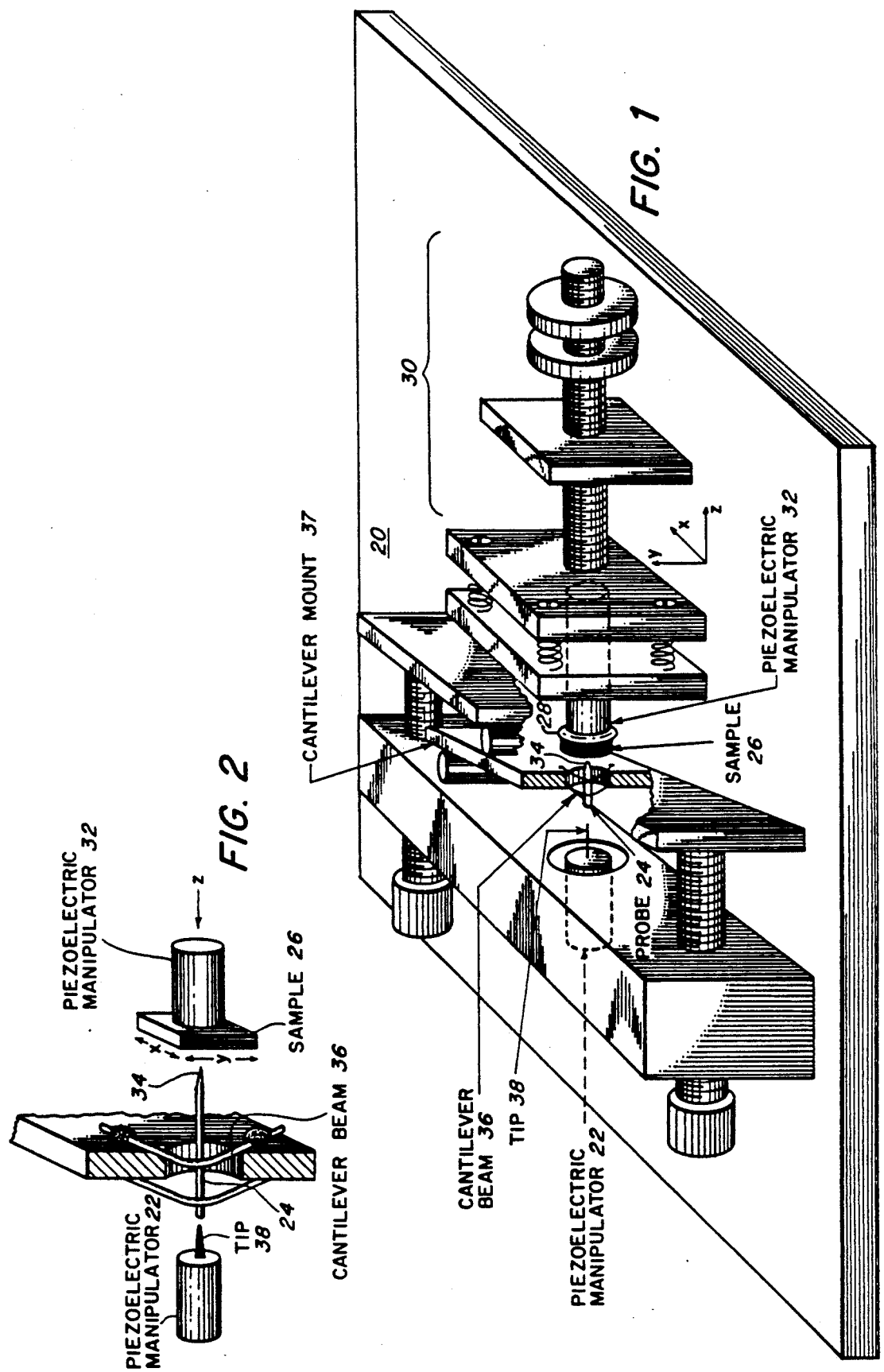

MECHANICAL AND SURFACE FORCE NANOPROBE

BACKGROUND OF THE INVENTION

1. Field of the Invention

This invention is in the field of measuring the surface forces and mechanical properties of materials; and, specifically, to measurements where nanoNewton (nN) forces, and less than nanometer (nm) distances must be resolved. Forces range from $10^{-3}$ to $10^{-9}$ Newtons and distances range from $10^{-6}$ to $10^{-10}$ meters. In addition to surface imaging, instruments of this type can be used to measure surface and mechanical properties of solid materials and the data from these surface measurements may be used to determine properties of materials such as hardness, elasticity, adhesion, surface tension, surface energy, and surface forces such as Van der Waals forces.

2. The Prior Art

This invention combines the capabilities of three different prior art instruments: the surface force apparatus, the hardness tester or indenter, and the atomic force microscope.

The surface force apparatus is used to study surface forces and adhesion. It consists of two crossed mica cylinders with radii of curvature on the order of 1 cm. One cylinder is in a fixed position; the other cylinder is suspended on a cantilever. The relative position of the cylinders, and thus the cantilever deflection, is determined by multi-beam interferometry. Using Hooke's Law ($F = -kz$), the interaction force between the cylinders is determined from the cantilever deflection times its effective spring constant. The surface force may be studied as a function of the distance between the cylinders. This technique is capable of measuring the separation of two surfaces to 0.2 nm but its lateral resolution is poor due to a contact area on the order of 10–30 $\mu m^2$. The force resolution, typically 10 nN, depends on the effective spring constant of the cantilever.

The hardness tester (also called a micro or nano indenter, materials tester, or mechanical properties microprobe) generates curves of force versus penetration depth. Mechanical properties of materials, such as elasticity and hardness, may be determined from the loading curves. After the indenter contacts the sample, the load (force) applied to the indenter tip causes the tip to penetrate into the sample surface. The applied load is plotted as a function of the penetration depth. Penetration depth resolution is as high as 0.4 nm. Force resolution with commercially available instruments is currently 300 nN; however, 100 nN. For comparison, this invention offers a force resolution of 1 nN and a depth resolution of 0.02 nm.

The atomic force microscope is used to image the surface of a sample with nanometer spatial resolution. As the sample moves under a probe mounted on a cantilever beam, the deflection of the beam determines the applied force. Beam deflection is measured by an electron tunneling microscope, optical measurements, or capacitance measurements. Plotting the cantilever deflection as a function of the sample's x and y position generates a nanometer-scale image. In the past, the atomic force microscope was used only for imaging.

BRIEF SUMMARY OF THE INVENTION

This invention uses an atomic force microscope as a surface force apparatus and a hardness tester. When used as instructed in this specification, an atomic force microscope is not only capable of providing nanometer-scale images of a surface, but also of measuring surface forces, mechanical, and adhesive properties of materials with a force, penetration depth, and spatial resolution superior to all other devices previously used. This differs from the atomic force microscope of the prior art because it provides for the measurement of surface deformations or surface positions as a function of the probe force exerted on a sample. It differs from the surface force apparatus in that it has high spatial resolution; it differs from the hardness tester in that it has much higher resolution of force and penetration depth, and in that it can image and measure surface forces and adhesion. In this invention, surface and materials properties are studied when the tip of a probe mounted onto a cantilever beam is brought close to and put into contact with the sample. The interaction of the probe and a sample surface can be used to measure (1) the elastic and plastic behavior and hardness of the sample by the indentation of the surface with a probe, (2) the long and short range forces (for example, Van der Walls, hydration, capillary, electrostatic, magnetic and capacitance forces) above the sample by positioning the probe tip 0.2–20 nm above the sample but not in contact with the sample, and (3) the adhesive forces, deformation mechanism, and fracture mechanics resulting from contact between the probe tip and sample during probe indentation and subsequent probe-sample separation.

In this invention, the instrument is configured to measure the force between a probe tip mounted on a cantilever beam and a point on a sample surface as a function of the sample to probe tip separation. This configuration allows studies of both the nano-mechanical properties of a sample and the forces associated with the probe tip-surface interaction.

These advantages result from the use of piezoelectric ceramics to accurately control the relative positions of the instrument's major components, the use of a flexible cantilever beam to accurately determine probe forces as a function of very small changes in displacement, and the use of electron tunneling to sense changes in the cantilever beam position.

Additional advantages and features will become apparent as the subject invention becomes better understood by reference to the following detailed description when considered in conjunction with the accompanying drawings.

BRIEF DESCRIPTION OF THE DRAWINGS

FIG. 1 is a schematic representation of the surface force measuring instrument of this invention.

FIG. 2 is an exploded view of the tunneling microscope tip, the cantilever beam, the probe and sample assembly.

DETAILED DESCRIPTION OF THE PREFERRED EMBODIMENT

Figure 3:
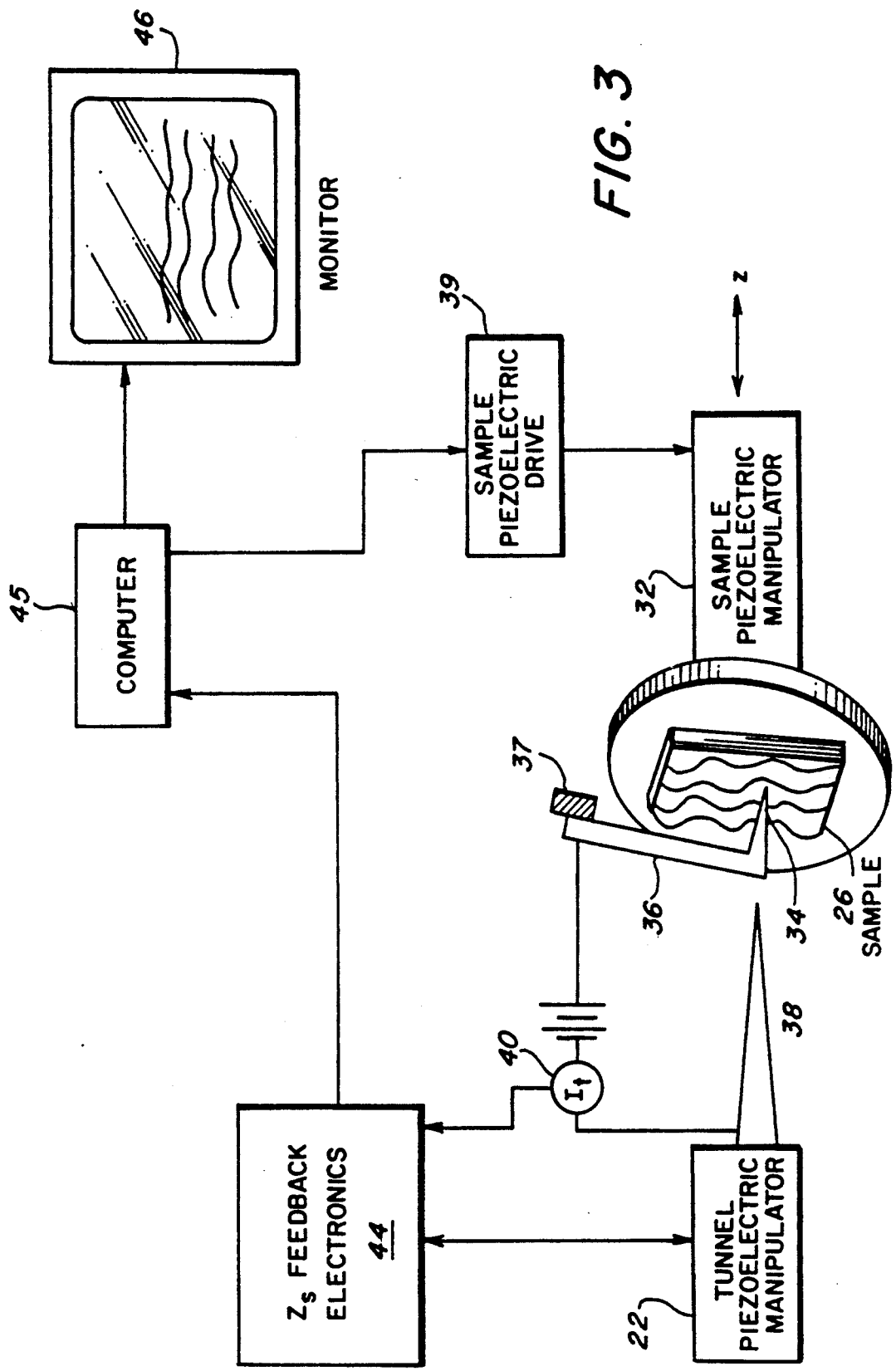
FIG. 3 is a schematic representation of a surface force measuring apparatus of this invention.

FIG. 1 is a schematic representation of the surface force sensor and indentation probe 20 of this invention. The left side shows the electron tunneling microscope or tunneling tip piezoelectric ceramic tube or tunneling tip piezoelectric manipulator 22 used to measure the deflection of probe 24 mounted in the center of a cantilever beam 36. The right side of FIG. 1 shows the sample stage comprising, sample holder 28 to which sample 26 attaches, coarse approach mechanism 30, and piezoelectric tube manipulator 32 which controls the x, y, and z motion of the sample. FIG. 2 is a schematic representation of the relationship among tunneling tip piezoelectric manipulator 22, probe 24, probe tip 34, sample 26, and sample piezoelectric manipulator 32.

Piezoelectric manipulator 22, 32 have electrodes to control the tube dimensions. The inside surface is covered by one electrode. The outer surface is divided among four equal areas along the major axis or the manipulator; each area is covered by one electrode. Piezoelectric manipulators 22, 32 change dimension when a voltage is applied across pairs of electrodes. This invention uses the manipulator's dimensional response to voltage to control the instrument movements. The voltages applied to manipulators 22, 32 are used to measure position and displacement within the instrument.

Cantilever beam 36 is made from small diameter tungsten wire. Probe 24 is made from thicker tungsten wire which is electrochemically etched to a small tip 34. The surface of probe 24 closest to tunneling tip 38 is coated with a thin layer of gold to resist oxidation thus preventing noise in the tunnel current. The force acting between probe tip 34 and sample 26 can be determined by measuring the displacement of cantilever beam 36. The separation between probe tip 34 and sample surface 26 is changed when sample piezoelectric drive circuit 39 (FIG. 3) changes the applied voltage thus causing the sample to move along the z axis. Displacement of cantilever 36 is measured by electron tunneling between the backside of probe 24 and electron tunneling tip 38. Electrons will tunnel across the gap between tip 38 and probe 24 when the two surfaces are less than 1 nm apart and a bias potential is applied. In FIG. 3, feedback control circuit 44 maintains a constant electron tunneling current 40 between tunneling tip 38 and cantilever beam 36. If an attractive force between probe tip 34 and sample surface 26 moves cantilever beam 36 towards sample 26, then the gap between the tunneling tip 38 and cantilever beam 36 will widen causing tunneling current 40 to decrease. Feedback control circuit 44 senses the change in current and changes the voltage applied to tunneling tip piezoelectric manipulator 22. This moves tunneling tip 38 closer to cantilever beam 36 re-establishing the constant electron tunneling current. Because feedback circuit 44 maintains a constant tunneling gap, and the distance the tunneling tip piezoelectric manipulator 22 moves is a function of the change in the voltage applied to ceramic 22, the change in applied voltage is a measure of the displacement of the cantilever beam 36.

Probe tip 34 and cantilever 36 may be constructed from different materials and with different geometries. The parallel structure shown for cantilever 36 constrains the motion of probe 24 to the z axis. The force laws governing the interaction between tip 34 and sample 26 are dependent on the tip geometry and on the interacting materials in tip 34 and sample 26.

Cantilever beam 36 may be made from various thicknesses or lengths of wire, configured in different ways. The effective spring constant of the cantilever beam may be altered by changing the wire's length, diameter, or configuration. The cantilever can also be micro-fabricated, using silicon etching or similar techniques. The cantilever may be mounted on a piezoelectric ceramic to control its position more precisely or to vibrate the cantilever at or near its resonance frequency in order to improve the sensitivity of force measurement.

Tunneling is the detection method shown in the preferred embodiment. However, other sufficiently sensitive means of detection include capacitance detection and optical means such as interferometry, optical position detection, and laser diodes.

In the preceding description piezoelectric manipulators 22, 32 are only subjected to direct current voltages. Alternatively, a small current oscillation may be applied to the z axis of one of the piezoelectric manipulators 22, 32 causing the data to be modulated by the applied frequency. This modulation detection scheme should reduce thermal drift problems.

An important advantage of this invention is that its improved force sensitivity and resolution allows surface measurements of any material, solid or liquid. Because the sample is not in the tunnel current conducting path, measurements can be made on insulating or conductive materials.

The device in FIG. 3 is capable of three different measurements: (1) surface force measurements, (2) indentation measurements, and (3) surface imaging. All of these measurements use active control of the z axis of the tunnel piezoelectric ceramic.

When surface force measurements are to be made, computer 45 provides a ramp signal causing piezoelectric drive 39 to apply a ramp voltage to the z axis of piezoelectric ceramic 32. The increasing voltage applied to its z axis causes the length of manipulator 32 to change, thus moving sample 26 towards cantilever 36 until probe tip 34 touches sample 26. The force on probe tip 38 is a known function of the deflection of beam 36. As their separation decreases, probe tip 34 is attracted to the surface of sample 26. Deflection of beam 36 is evidenced by the change in the voltage applied to tunneling piezoelectric manipulator 22. After contact, probe tip 34 is moved in the opposite direction, that is towards tunnel tip 38, by the continued travel of sample 26. Adhesive forces are computed from the deflection of beam 36 required to break contact as sample 26 is withdrawn.

Indentation measurements are made using the same procedure used in the surface force measurement. After probe 24 and sample surface 26 contact, the depth that probe tip 34 penetrates into sample 26 is then computed from the difference in movement of sample 26 and probe tip 34. These movements are known as a function of the change in voltages applied to piezoelectric manipulator 22, 32.

The force acting between probe tip 34 and sample 26 can be determined by measuring the displacement of cantilever beam 36. The separation between probe tip 34 and sample surface 26 is changed when sample piezoelectric drive circuit 39 (FIG. 3) changes the applied voltage thus causing the sample to move along the z axis. Displacement of cantilever 36 is measured by electron tunneling between the backside of probe 24 and electron tunneling tip 38. Electrons will tunnel across the gap between tip 38 and probe 24 when the two surfaces are less than 1nm apart and a bias potential is applied. In FIG. 3, feedback control circuit 44 maintains a constant electron tunneling current 40 between tunneling tip 38 and cantilever beam 36. If an attractive force between the probe tip 34 and sample surface 26 moves cantilever beam 36 towards sample 26, then the gap between the tunneling tip 38 and cantilever beam 36 will widen causing tunneling current 40 to decrease.

Feedback control circuit 44 senses the change in current and changes the voltage applied to tunneling tip piezoelectric manipulator 22. This moves tunneling tip 38 closer to cantilever beam 36 reestablishing the constant electron tunneling current. Because feedback circuit 44 maintains a constant tunneling gap, the distance the tunneling tip piezoelectric manipulator 22 moves is a function of the change in the voltage applied to manipulator 22, the change in applied voltage is a measure of the displacement of the cantilever beam 36.

The x-y translation of the sample allows multiple tests to be performed on each sample surface.

When used in the traditional imaging mode, the sample is moved in the x and y directions while the cantilever position is measured by the voltage applied to piezoelectric manipulator 22. Current 40, $I_t$, is held constant, as explained above, by controlling the position of tunneling tip 38. As the tunneling current 40 is held constant, the tunneling distance is held constant. The required change in z axis voltage applied to piezoelectric rides on the surface of sample 26. Cantilever motion is plotted against the sample's x-y position to generate a nanometer-scale image of the sample surface.

Experimental surface force and indentation measurements of different surfaces, including monolayer films, are reported in MEASURING THE NANOMECHANICAL PROPERTIES AND SURFACE FORCES OF MATERIALS USING AN ATOMIC FORCE MICROSCOPE, N. Burnham and R. Colton; J. Vac. Sci. Technol., A7 (4), page 2906, Jul/Aug 1989; and PROBING THE SURFACE FORCES OF MONOLAYER FILMS WITH AN ATOMIC-FORCE MICROSCOPE, N. Burnham, D. Dominguez, R. Mowery, and R. Colton; Physical Review Letters, Volume 64, Number 16, page 1931, Apri. 16, 1990.

Although the best mode of the invention has been described, it should be understood that changes and deletions in the detail can be made without departing from the spirit and scope of this invention.

What is claimed is:

1. A method for using an Atomic Force Microscope (AFM) to measure a surface property of a sample, comprising:
   mounting a probe for said AFM on a cantilever whose deflection is a function of the force applied to said probe;
   placing said probe and said sample at a separation greater than the zero deflection range of said surface property to be measured;
   reducing said separation to zero by moving said sample towards said probe;
   using a deflection measuring means to measure said deflection of said cantilever as a function of the position of said sample; and
   determining said surface property of said sample from said displacement.

2. The method of claim 1 wherein said deflection measuring means is electron tunneling.

3. The method of claim 1 wherein said deflection measuring means is an optical means.

4. The method of claim 1 wherein said deflection measuring means is a capacitance measuring means.

5. A method as in claim 1 wherein said measurement of a surface property, comprises the steps of;
   reversing the direction of travel of said sample until contact with said probe is broken;
   determining surface force at each of a plurality of separations between the point of contact and the zero deflation separation from the measured deflection at that separation; and
   recording surface force versus said separation.

6. A method as in claim 1 wherein said determining step comprises the steps of;
   determining the penetration of the probe into the sample from the relative motion of the probe and the sample;
   reversing the direction of travel of the sample until contact with the probe is broken;
   determining the applied force by applying the deflection function to the measured deflection; and
   recording the penetration versus the applied force.

* * * * *